United States Patent [19]
Köster et al.

[11] Patent Number: 5,928,906
[45] Date of Patent: Jul. 27, 1999

[54] PROCESS FOR DIRECT SEQUENCING DURING TEMPLATE AMPLIFICATION

[75] Inventors: Hubert Köster, Concord, Mass.; Dirk Van Den Boom, Dreieich; Andreas Ruppert, Linden, both of Germany

[73] Assignee: Sequenom, Inc., San Diego, Calif.

[21] Appl. No.: 08/647,368

[22] Filed: May 9, 1996

[51] Int. Cl.⁶ .......................... C12P 19/34; C07H 21/04; C07H 21/00; C25B 1/00

[52] U.S. Cl. .............................. 435/91.2; 435/6; 435/395; 435/91.1; 204/182.8; 250/281; 250/282; 536/243; 536/25.3; 935/77

[58] Field of Search ............................... 435/91.2, 6, 395, 435/91.1; 204/182.8; 536/24.3, 25.3; 250/281, 282; 935/77

[56] References Cited

U.S. PATENT DOCUMENTS

| | | | |
|---|---|---|---|
| 5,003,059 | 3/1991 | Brennan | 536/27 |
| 5,108,892 | 4/1992 | Burke et al. | 435/6 |
| 5,427,911 | 6/1995 | Ruano | 525/54.11 |

FOREIGN PATENT DOCUMENTS

| | | | |
|---|---|---|---|
| WO 93/02212 | 2/1993 | WIPO | C12Q 1/68 |
| WO 93/06243 | 4/1993 | WIPO | C12Q 1/68 |
| WO 94/16101 | 7/1994 | WIPO | C12Q 1/68 |

OTHER PUBLICATIONS

Murray, V., "Improved Double–Stranded DNA Sequencing Using the Linear Polymerase Chain Reaction", *Nucleic Acids Research*, vol. 17, No. 21, 8889 (1989).

Redstone, M. et al., "Klenow Co–Sequencing: A Method for Eliminating "Stops"", *Biotechniques*, vol. 17, No. 2, 286, 288 (1994).

Schneider, K. et al., "Increased Stability of Nucleic Acids Containing 7–deaza–guanosine and 7–deaza–adenosine May Enable Rapid DNA Sequencing By Matrix–assisted Laser Desorption Mass Spectrometry", *Nucleic Acids Research*, vol. 23, No. 9, 1570–1575 (1995); and.

International Search Report (PCT/US97/07966) Sep. 19, 1997.

Reston et al. klenow Co–Sequencing; A method for Eliminating "Stops", BioTechniques, vol. 17(2), p. 268, 1994.

Skerra Phosphorothioate Primers Improve the amplification of DNA Sequence by DNA Polymerases with Proofreading Activity, Nucleic Acids Research, vol. 20 (4), pp. 3551–3554, 1992.

Bell, J., "The Polymerase Chain Reaction," *Immunology Today*, vol. 10, No. 10, 351–355 (1989).

Gibbs, R., "DNA Amplification by the Polymerase Chain Reaction," *Anal. Chem.*, vol. 62, 1202–1214 (1990).

Martin, W., "New Technologies for Large–genome Sequencing," *Genome*, vol. 31, 1073–1080 (1989).

Templeton, N., "The Polymerase Chain Reaction: History, Methods, and Applications," *Diagnostic Molecular Pathology*, vol. 1, No. 1, 58–72 (1992).

Walker, G. "Multiplex Strand Displacement Amplification (SDA) and Detection of DNA Sequences from *Mycobacterium tuberculosis* and Other Mycobacteria," *Nucleic Acids Research*, vol. 22, No. 13, 2670–2677 (1994).

*Primary Examiner*—Kenneth R. Horlick
*Assistant Examiner*—Joyce Tung
*Attorney, Agent, or Firm*—Beth E. Arnold; Foley, Hoag & Eliot LLP

[57] ABSTRACT

Processes and kits for simultaneously amplifying and sequencing nucleic acid molecules, and perfonning high throughput DNA sequencing are described.

48 Claims, 2 Drawing Sheets

PROCESS FOR DIRECT SEQUENCING DURING TEMPLATE AMPLIFICATION

BACKGROUND OF THE INVENTION

DNA Sequencing

Current knowledge regarding gene structure, the control of gene activity and the function of cells on a molecular level all arose based on the determination of the base sequence of millions of DNA molecules. DNA sequencing is still critically important in research and for genetic therapies and diagnostics, (e.g., to verify recombinant clones and mutations).

DNA, a polymer of deoxyribonucleotides, is found in all living cells and some viruses. DNA is the carrier of genetic information, which is passed from one generation to the next by homologous replication of the DNA molecule. Information for the synthesis of all proteins is encoded in the sequence of bases in the DNA.

To obtain the genetic information and therefore to reveal the base sequence of a given DNA molecule, chemical and enzymatic sequencing methods have been developed. DNA-sequencing as proposed by Maxam-Gilbert (Maxam, A. M., W. Gilbert, Proc. Natl. Acad. Sci. USA, 74:560–564 1977) is a chemical method of determining base composition of a nucleic acid molecule. A single stranded DNA molecule with radioactive label at its 5' end is chemically modified in four base specific reactions and then cleaved at the modified positions. The cleavage products are separated on a polyacrylamide gel and typically are detected by autoradiography.

Currently favoured is the enzymatic chain termination reaction according to the Sanger-sequencing method (Sanger, F. et. al., Proc. Natl. Acad. Sci. USA, 74:5463–5467 1977). In the Sanger method, the four base specific sets of DNA fragments are formed by starting with a primer/template system elongating the primer into the unknown DNA sequence area and thereby copying the template and synthesizing complementary strands using a DNA polymerase in the presence of chain-terminating reagents. The chain-terminating event is achieved by incorporating into the four separate reaction mixtures in addition to the four normal deoxynucleoside triphosphates, dATP, dGTP, dTTP and dCTP, only one of the chain-terminating dideoxynucleoside triphosphates, ddATP, ddGTP, ddTTP or ddCTP, respectively in a limiting small concentration. The incorporation of a ddNTP lacking the 3' hydroxyl function into the growing DNA strand by the enzyme DNA polymerase leads to chain termination through preventing the formation of a 3'-5'-phosphodiester bond by DNA polymerase. Due to the random incorporation of the ddNTPs, each reaction leads to a population of base specific terminated fragments of different lengths, which all together represent the sequenced DNA-molecule.

A recent modification of the Sanger sequencing strategy involves the degradation of phosphorothioate-containing DNA fragments obtained by using alpha-thio dNTP instead of the normally used ddNTPs during the primer extension reaction mediated by DNA polymerase (Labeit et al., *DNA* 5, 173–177 (1986); Amersham, PCT-Application GB86/00349; Eckstein et al., *Nucleic Acids Res.* 16, 9947 (1988)). Here, the four sets of base-specific sequencing ladders are obtained by limited digestion with exonuclease III or snake venom phosphodiesterase, subsequent separation on PAGE and visualization by radioisotopic labeling of either the primer or one of the dNTPs. In a further modification, the base-specific cleavage is achieved by alkylating the sulphur atom in the modified phosphodiester bond followed by a heat treatment (Max-Planck-Gesellschaft, DE 3930312 A1).

DNA Amplification

DNA can be amplified by a variety of procedures including cloning (Sambrook et al., Molecular Cloning: A Laboratory Manual, Cold Spring Harbor Laboratory Press, 1989), polymerase chain reaction (PCR) (C. R. Newton and A. Graham, PCR, BIOS Publishers, 1994), ligase chain reaction (LCR) (F. Barany *Proc. Natl. Acad. Sci USA* 88, 189–93 (1991), strand displacement amplification (SDA) (G. Terrance Walker et al., *Nucleic Acids Res.* 22, 2670–77 (1994)) and variations such as RT-PCR, allele-specific amplification (ASA) etc.

The polymerase chain reaction (Mullis, K. et al., Methods Enzymol., 155:335–350 1987) permits the selective in vitro amplification of a particular DNA region by mimicking the phenomena of in vivo DNA replication. Required reaction components are single stranded DNA, primers (oligonucleotide sequences complementary to the 5' and 3' ends of a defined sequence of the DNA template), deoxynucleotidetriphosphates and a DNA polymerase enzyme. Typically, the single stranded DNA is generated by heat denaturation of provided double strand DNA. The reaction buffers contain magnesium ions and co-solvents for optimum enzyme stability and activity.

The amplification results from a repetition of such cycles in the following manner: The two different primers, which bind selectively each to one of the complementary strands, are extended in the first cycle of amplification. Each newly synthesized DNA then contains a binding site for the other primer. Therefore each new DNA strand becomes a template for any further cycle of amplification enlarging the template pool from cycle to cycle. Repeated cycles theoretically lead to exponential synthesis of a DNA-fragment with a length defined by the 5' termini of the primer.

Initial PCR experiments used thermolabile DNA polymerase. However, thermolabile DNA polymerase must be continually added to the reaction mixture after each denaturation cycle. Major advances in PCR practice were the development of a polymerase, which is stable at the near-boiling temperature (Saiki, R. et al., Science 239:487–491 1988) and the development of automated thermal cyclers.

The discovery of thermostable polymerases also allowed modification of the Sanger sequencing reaction with significant advantages. The polymerization reaction could be carried out at high temperature with the use of thermostable DNA polymerase in a cyclic manner (cycle sequencing). The conditions of the cycles are similar to those of the PCR technique and comprise denaturation, annealing, and extension steps. Depending on the length of the primers only one annealing step at the beginning of the reaction may be sufficient. Carrying out a sequencing reaction at high temperature in a cyclic manner provides the advantage that each DNA strand can serve as template in every new cycle of extension which reduces the amount of DNA necessary for sequencing, thereby providing access to minimal volumes of DNA, as well as resulting in improved specificity of primer hybridisation at higher temperature and the reduction of secondary structures of the template strand.

However, amplification of the terminated fragments is linear in conventional cycle sequencing approaches. A recently developed method, called semi-exponential cycle sequencing shortens the time required and increases the extent of amplification obtained from conventional cycle sequencing by using a second reverse primer in the sequencing reaction. However, the reverse primer only generates additional template strands if it avoids being terminated prior to reaching the sequencing primer binding site. Needless to say, terminated fragments generated by the reverse primer can not serve as a sufficient template. Therefore, in practice, amplification by the semi-exponential approach is not entirely exponential. (Sarkat, G. and Bolander Mark E., Semi Exponential Cycle Sequencing Nucleic Acids Research, 1995, Vol. 23, No. 7, p. 1269–1270).

As pointed out above, current nucleic acid sequencing methods require relatively large amounts (typically about 1 μg) of highly purified DNA template. Often, however, only a small amount of template DNA is available. Although amplifications may be performed, amplification procedures are typically time consuming, can be limited in the amount of amplified template produced and the amplified DNA must be purified prior to sequencing. A streamlined process for amplifying and sequencing DNA is needed, particularly to facilitate highthroughput nucleic acid sequencing.

SUMMARY OF THE INVENTION

In general, the instant invention provides a one-step process for generating from a DNA template, base specifically terminated fragments of sufficient quantity to enable DNA sequencing.

According to the process of the invention, a combined amplification and termination reaction is performed using at least two different polymerase enzymes, each having a different affinity for the chain terminating nucleotide, so that polymerization by an enzyme with relatively low affinity for the chain terminating nucleotide leads to exponential amplification whereas an enzyme with relatively high affinity for the chain terminating nucleotide terminates the polymerization and yields sequencing products.

In another aspect, the invention features kits for directly amplifying nucleic acid templates and generating base specifically terminated fragments. In one embodiment, the kit can comprise an appropriate amount of: i) a complete set of chain-elongating nucleotides; ii) at least one chain-terminating nucleotide; (iii) a first DNA polymerase, which has a relatively low affinity towards the chain terminating nucleotide; and (iv) a second DNA polymerase, which has a relatively high affinity towards the chain terminating nucleotide. The kit can also optionally include an appropriate primer or primers, appropriate buffers as well as instructions for use.

The instant invention allows DNA amplification and termination to be performed in one reaction vessel. Due to the use of two polymerases with different affinities for dideoxy nucleotide triphosphates, exponential amplification of the target sequence can be accomplished in combination with a termination reaction nucleotide. In addition, the process obviates the purification procedures, which are required when amplification is performed separately from base terminated fragment generation. Further, the instant process requires less time to accomplish than separate amplification and base specific termination reactions.

When combined with a detection means, the process can be used to detect and/or quantitate a particular nucleic acid sequence where only small amounts of template are available and fast and accurate sequence data acquisition is desirable. For example, when combined with a detection means, the process is useful for sequencing unknown genes or other nucleic acid sequences and for diagnosing or monitoring certain diseases or conditions, such as genetic diseases, chromosomal abnormalities, genetic predispositions to certain diseases (e.g. cancer, obesity, artherosclerosis) and pathogenic (e.g. bacterial, viral, fungal, protistal) infections. Further, when double stranded DNA molecules are used as the starting material, the instant process provides an opportunity to simultaneously sequence both strands, thereby providing greater certainty of the sequence data obtained or acquiring sequence information from both ends of a longer template.

The above and further features and advantages of the instant invention will become clearer from the following Detailed Description and Claims.

DETAILED DESCRIPTION OF THE INVENTION

Figure 1:
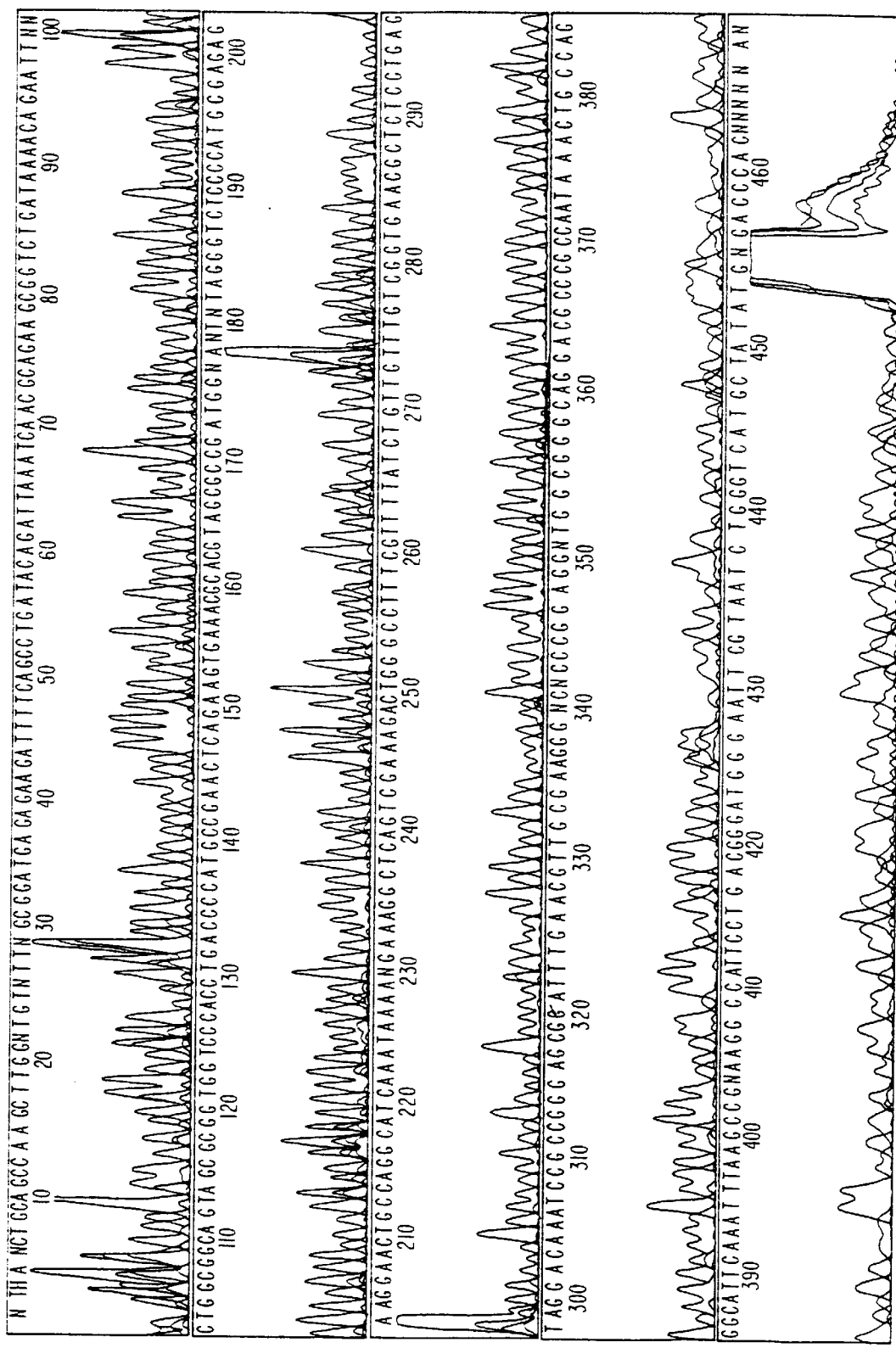
FIG. 1 shows sequence data from an ABI-Prism automated sequencer (Model 373A) using a p0M8 derived recombinant plasmid with a 400 base pair (BP) insert from the rrnB gene of *E. coli* as the template in the reaction described in the following Example 1. The figure shows a reliable sequence readable to about 440 BP which is the length of the PCR product.

In general, the invention features a process for directly amplifying and base specifically terminating a nucleic acid molecule. According to the process of the invention, a combined amplification and termination reaction is performed on a nucleic acid template using: i) a complete set of chain-elongating nucleotides; ii) at least one chain-terminating nucleotide; and (iii) a first DNA polymerase, which has a relatively low affinity towards the chain terminating nucleotide; and (iv) a second DNA polymerase, which has a relatively high affinity towards the chain terminating nucleotide, so that polymerization by the enzyme with relatively low affinity for the chain terminating nucleotide leads to amplification of the template, whereas the enzyme with relatively high affinity for the chain terminating nucleotide terminates the polymerization and yields sequencing products.

The combined amplification and sequencing can be based on any amplification procedure that employs an enzyme with polynuclcotide synthetic ability (e.g. polymerase). One preferred process, based on the polymerase chain reaction (PCR), is comprised of the following three thermal steps: 1) denaturing a double stranded (ds) DNA molecule at an appropriate temperature and for an appropriate period of time to obtain the two single stranded (ss) DNA molecules (the template: sense and antisense strand); 2) contacting the template with at least one primer that hybridizes to at least one ss DNA template at an appropriate temperature and for an appropriate period of time to obtain a primer containing ss DNA template; 3) contacting the primer containing template at an appropriate temperature and for an appropriate period of time with: (i) a complete set of chain elongating nucleotides, (ii) at least one chain terminating nucleotide, (iii) a first DNA polymerase, which has a relatively low affinity towards the chain terminating nucleotide; and (iv) a second DNA polymerase, which has a relatively high affinity towards the chain terminating nucleotide.

Steps 1)–3) can be sequentially performed for an appropriate number of times (cycles) to obtain the desired amount of amplified sequencing ladders. The quantity of the base specifically terminated fragment desired dictates how many cycles are performed. Although an increased number of cycles results in an increased level of amplification, it may also detract from the sensitivity of a subsequent detection. It is therefore generally undesirable to perform more than about 50 cycles, and is more preferable to perform less than about 40 cycles (e.g. about 20–30 cycles).

In a preferred embodiment, the first denaturation step is performed at a temperature in the range of about 85° C. to about 100° C. (most preferably about 92° C. to about 96° C.) for about 20 seconds (s) to about 2 minutes (most preferably about 30 s–1 minute). The second hybridization step is preferably performed at a temperature, which is in the range of about 40° C. to about 80° C. (most preferably about 45° C. to about 72° C.) for about 20 s to about 2 minutes (most preferably about 30 s–1 minute). The third, primer extension step is preferably performed at about 65° C. to about 80° C. (most preferably about 70° C. to about 74° C.) for about 30 s to about 3 minutes (most preferably about 1 to about 2 minutes).

In order to obtain sequence information on both the sense and antisense strands of a DNA molecule simultaneously, each of the single stranded sense and antisense templates generated from the denaturing step can be contacted with appropriate primers in step 2), so that amplified and chain terminated nucleic acid molecules generated in step 3), are complementary to both strands.

Another preferred process for simulataneously amplifying and chain terminating a nucleic acid sequence is based on strand displacement amplification (SDA) (G. Terrance Walker et al., *Nucleic Acids Res.* 22, 2670–77 (1994); European Patent Publication Number 0 684 315 entitled *Strand Displacement Amplification Using Thermophilic Enzymes*). In essence, this process involves the following three steps, which altogether comprise a cycle: 1) denaturing a double stranded (ds) DNA molecule containing the sequence to be amplified at an appropriate temperature and for an appropriate period of time to obtain the two single stranded (ss) DNA molecules (the template: sense and antisense strand); 2) contacting the template with at least one primer (P), that contains a recognition/cleavage site for a restriction endonuclease (RE) and that hybridizes to at least one ss DNA template at an appropriate temperature and for an appropriate period of time to obtain a primer containing ss DNA template; 3) contacting the primer containing template at an appropriate temperature and for an appropriate period of time with: (i) a complete set of chain elongating nucleotides; (ii) at least one chain terminating nucleotide, (iii) a first DNA polymerase, which has a relatively low affinity towards the chain terminating nucleotide; (iv) a second DNA polymerase, which has a relatively high affinity towards the chain terminating nucleotide; and v) an RE that nicks the primer recognition/cleavage site.

Steps 1)–3) can be sequentially performed for an appropriate number of times (cycles) to obtain the desired amount of amplified sequencing ladders. As with the PCR based process, the quantity of the base specifically terminated fragment desired dictates how many cycles are performed. Preferably, less than 50 cycles, more preferably less than about 40 cycles and most preferably about 20 to 30 cycles are performed.

The amplified sequencing ladders obtained as described above, can be separated and detected and/or quantitated using well established methods, such as polyacrylamide gel electrophoresis (PAGE), or capillary zone electrophoresis (CZE) (Jorgenson et al., *J. Chromatography* 352, 337 (1986); Gesteland et al., *Nucleic Acids Res.* 18, 1415–1419 (1990)); or direct blotting electrophoresis (DBE) (Beck and Pohl, *EMBO J*, vol. 3: Pp. 2905–2909 (1984)) in conjunction with, for example, colorimetry, fluorimetry, chemiluminescence and radioactivity.

When mass spectrometry is used in conjunction with the direct amplification and chain termination processes, the sequencing ladders can be directly detected without first being separated using several mass spectrometer formats. Amenable formats for use in the invention include ionization techniques such as matrix-assisted laser desorption (MALDI), continuous or pulsed electrospray (ESI) and related methods (e.g. Ionspray or Thermospray), and massive cluster impact (MSI); these ion sources can be matched with a detection format, such as linear or reflectron time-of-flight (TOF), single or multiple quadrupole, single or multiple magnetic sector, Fourier Transform ion cyclotron resonance (FTICR), ion trap, or combinations of these to give a hybrid detector (e.g. ion trap-TOF). For ionization, numerous matrix/wavelength combinations (MALDI) or solvent combinations (ESI) can be employed.

The above-described process can be performed using virtually any nucleic acid molecule as the source of the DNA template. For example, the nucleic acid molecule can be: a) single stranded or double stranded; b) linear or covalently closed circular in supercoiled or relaxed form; or c) RNA if combined with reverse transcription to generate a CDNA. For example, reverse transcription can be performed using a suitable reverse transcriptase (e.g. Moloney murine leukemia virus reverse transcriptase) using standard techniques (e.g. Kawasaki (1990) in *PCR Protocols: A Guide to Methods and Applications*, Innis et al., eds., Academic Press, Berkeley, Calif. pp21–27).

Sources of nucleic acid templates can include: a) plasmids (naturally occurring or recombinant); b) RNA- or DNA-viruses and bacteriophages (naturally occurring or recombinant); c) chromosomal or episomal replicating DNA (e.g. from tissue, a blood sample, or a biopsy); d) a nucleic acid fragment (e.g. derived by exonuclease, unspecific endonuclease or restriction endonuclease digestion or by physical disruption (e.g. sonication or nebulization)); and e) RNA or RNA transcripts like mRNAs.

The nucleic acid to be amplified and sequenced can be obtained from virtually any biological sample. As used herein, the term "biological sample" refers to any material obtained from any living source (e.g. human, animal, plant, bacteria, fungi, protist, virus). Examples of appropriate biological samples for use in the instant invention include: solid materials (e.g tissue, cell pellets, biopsies) and biological fluids (e.g. urine, blood, saliva, amniotic fluid, mouth wash, spinal fluid). The nucleic acid to be amplified and sequenced can be provided by unpurified whole cells, bacteria or virus. Alternatively, the nucleic acid can first be purified from a sample using standard techniques, such as: a) cesium chloride gradient centrifugation; b) alkaline lysis with or without RNAse treatment; c) ion exchange chromatography; d) phenol/chloroform extraction; e) isolation by hybridization to bound oligonucleotides; f) gel electrophoresis and elution; alcohol precipitation and h) combinations of the above.

As used herein, the phrases "chain-elongating nucleotides" and "chain-terminating nucleotides" are used in accordance with their art recognized meaning. For example, for DNA, chain-elongating nucleotides include 2'-deoxyribonucleotides (e.g. dATP, dCTP, dGTP and dTTP)

and chain-terminating nucleotides include 2', 3'- dideoxyribonucleotides (e.g. ddATP, ddCTP, ddGTP, ddTTP). For RNA, chain-elongating nucleotides include ribonucleotides (e.g., ATP, CTP, GTP and UTP) and chain-terminating nucleotides include 3'-deoxyribonucleotides (e.g. 3'dA, 3'dC, 3'dG and 3'dU). A complete set of chain elongating nucleotides refers to dATP, dCTP, dGTP and dTTP. The term "nucleotide" is also well known in the art. For the purposes of this invention, nucleotides include nucleoside mono-, di-, and triphosphates. Nucleotides also include modified nucleotides such as phosphorothioate nucleotides and deazapurine nucleotides. A complete set of chain-elongating nucleotides refers to four different nucleotides that can hybridize to each of the four different bases comprising the DNA template.

If the amplified sequencing ladders are to be detected by mass spectrometric analysis, it may be useful to "condition" nucleic acid molecules, for example to decrease the laser energy required for volatization and/or to minimize fragmentation. Conditioning is preferably performed while the sequencing ladders are immobilized. An example of conditioning is modification of the phosphodiester backbone of the nucleic acid molecule (e.g. cation exchange), which can be useful for eliminating peak broadening due to a heterogeneity in the cations bound per nucleotide unit. Contacting a nucleic acid molecule, which contains an α-thio-nucleoside-triphosphate during polymerization with an alkylating agent such as akyliodide, iodoacetamide, β-iodoethanol, or 2,3-epoxy-1-propanol, the mononothio phosphodiester bonds of a nucleic acid molecule can be transformed into a phosphotriester bond. Further conditioning involves incorporating nucleotides which reduce sensitivity for depurination (fragmentation during MS), e.g. a purine analog such as N7- or N9-deazapurine nucleotides, and partial RNA containing oligodeoxynucleotide to be able to remove the unmodified primer from the amplified and modified sequencing ladders by RNAse or alkaline treatment. In DNA sequencing using fluorescent detection and gel electrophoretic separation, the N7 deazapurine nucleotides reduce the formation of secondary structure resulting in band compression from which no sequencing information can be generated.

Critical to the novel process of the invention is the use of appropriate amounts of two different polymerase enzymes, each having a different affinity for the particular chain terminating nucleotide, so that polymerization by the enzyme with relatively low affinity for the chain terminating nucleotide leads to amplification whereas the enzyme with relatively high affinity for the chain terminating nucleotide terminates the polymerization and yields sequencing products. Preferably about 0.5 to about 3 units of polymerase is used in the combined amplification and chain termination reaction. Most preferably about 1 to 2 units is used. Particularly preferred polymerases for use in conjunction with PCR or other thermal amplification process are thermostable polymerases, such as Taq DNA polymerase (Boehringer Mannheim), AmpliTaq FS DNA polymerase (Perkin-Elmer), Deep Vent (exo-), Vent, Vent (exo-) and Deep Vent DNA polymerases (New England Biolabs), Thermo Sequenase (Amersham) or exo(-) *Pseudococcus furiosus* (Pfu) DNA polymerase (Stratagene, Heidelberg Germany). AmpliTaq, Ultman, 9 degree Nm, Tth, Hot Tub, and *Pyrococcus furiosus*. In addition, preferably the polymerase does not have 5'-3'exonuclease activity.

As shown in Example 1, the process of the invention can be carried out using AmpliTaq FS DNA polymerase (Perkin-Elmer), which has a relatively high affinity and Taq DNA polymerase, which has a relatively low affinity for chain terminating nucleotides. Other appropriate polymerase pairs for use in the instant invention can be determined by one of skill in the art. (See e.g. S. Tabor and C. C. Richardson (1995) *Proc. Nat. Acad. Sci.* (USA), vol. 92: Pp. 6339–6343.)

In addition to polymerases, which have a relatively high and a relatively low affinity to the chain terminating nucleotide, a third polymerase, which has proofreading capacity (e.g. *Pyrococcus woesei* (Pwo)) DNA polymerase may also be added to the amplification mixture to enhance the fidelity of amplification.

Oligonucleotide primers, for use in the invention, can be designed based on knowledge of the 5' and/or 3' regions of the nucleotide sequence to be amplified and sequenced, e.g., insert flanking regions of cloning and sequencing vectors (such as M13, pUC, phagemid, cosmid). Optionally, at least one primer used in the chain extension and termination reaction can be linked to a solid support to facilitate purification of amplified product from primers and other reactants, thereby increasing yield or to separate the Sanger ladders from the sense and antisense template strand where simultaneous amplification-sequencing of both a sense and antisense strand of the template DNA has been performed.

Examples of appropriate solid supports include beads (silica gel, controlled pore glass, magnetic beads, Sephadex/Sepharose beads, cellulose beads, etc.), capillaries, flat supports such as glass fiber filters, glass surfaces, metal surfaces (steel, gold, silver, aluminum, and copper), plastic materials or membranes (polyethylene, polypropylene, polyamide, polyvinylidenedifluoride) or beads in pits of flat surfaces such as wafers (e.g. silicon wafers), with or without filter plates.

Immobilization can be accomplished, for example, based on hybridization between a capture nucleic acid sequence, which has already been immobilized to the support and a complementary nucleic acid sequence, which is also contained within the nucleic acid molecule containing the nucleic acid sequence to be detected. So that hybridization between the complementary nucleic acid molecules is not hindered by the support, the capture nucleic acid can include a spacer region of at least about five nucleotides in length between the solid support and the capture nucleic acid sequence. The duplex formed will be cleaved under the influence of the laser pulse and desorption can be initiated. The solid support-bound base sequence can be presented through natural oligoribo- or oligodeoxyribo- nucleotide as well as analogs (e.g. thio-modified phosphodiester or phosphotriester backbone) or employing oligonucleotide mimetics such as PNA analogs (see e.g. Nielsen et al., *Science,* 254, 1497 (1991)) which render the base sequence less susceptible to enzymatic degradation and hence increases overall stability of the solid support-bound capture base sequence.

Alternatively, a target detection site can be directly linked to a solid support via a reversible or irreversible bond between an appropriate functionality (L') on the target nucleic acid molecule and an appropriate functionality (L) on the capture molecule. A reversible linkage can be such that it is cleaved under the conditions of mass spectrometry (i.e., a photocleavable bond such as a trityl ether bond or a charge transfer complex or a labile bond being formed between relatively stable organic radicals). Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L,' by specific absorption of laser energy which is in resonance with the L' chromophore.

By way of example, the L–L' chemistry can be of a type of disulfide bond (chemically cleavable, for example, by mercaptoethanol or dithioerythrol), a biotin/streptavidin system, a heterobifunctional derivative of a trityl ether group (Köster et al., "A Versatile Acid-Labile Linker for Modification of Synthetic Biomolecules," *Tetrahedron Letters* 31, 7095 (1990)) which can be cleaved under mildly acidic conditions as well as under conditions of mass spectrometry, a levulinyl group cleavable under almost neutral conditions with a hydrazinium/acetate buffer, an arginine—arginine or lysine—lysine bond cleavable by an endopeptidase enzyme like trypsin or a pyrophosphate bond cleavable by a pyrophosphatase or a ribonucleotide in between a deoxynucleotide sequence cleavable by an RNAse or alkali.

The functionalities, L and L,' can also form a charge transfer complex and thereby form the temporary L–L' linkage. Since in many cases the "charge-transfer band" can be determined by UV/vis spectrometry (see e.g. *Organic Charge Transfer Complexes* by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L–L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g. *Reactive Molecules* by C. Wentrup, John Wiley & Sons, 1984).

An anchoring function L' can also be incorporated into a target capturing sequence by using appropriate primers during an amplification procedure, such as PCR, LCR or transcription amplification.

For certain applications, it may be useful to simultaneously amplify and chain terminate more than one (mutated) loci on a particular captured nucleic acid fragment (on one spot of an array) or it may be useful to perform parallel processing by using oligonucleotide or oligonucleotide mimetic arrays on various solid supports. "Multiplexing" can be achieved either by the sequence itself (composition or length) or by the introduction of mass-modifying functionalities into the primer oligonucleotide. Such multiplexing is particularly useful in conjunction with mass spectrometric DNA sequencing or mobility modified gel based fluorescence sequencing.

Without limiting the scope of the invention, the mass or mobility modification can be introduced by using oligo-/polyethylene glycol derivatives. The oligo/polyethylene glycols can also be monoalkylated by a lower alkyl such as methyl, ethyl, propyl, isopropyl, t-butyl and the like. Other chemistries can be used in the mass-modified compounds, as for example, those described recently in *Oligonucleotides and Analogues, A Practical Approach*, F. Eckstein, editor IRL, Press, Oxford, 1991.

In yet another embodiment, various mass or mobility modifying functionalities, other than oligo/polyethylene glycols, can be selected and attached via appropriate linking chemistries. A simple modification can be achieved by using different alkyl, aryl or aralkyl moieties such as methyl, ethyl, propyl, isopropyl, t-butyl, hexyl, phenyl, substituted phenyl or benzyl. Yet another modification can be obtained by attaching homo- or heteropeptides to the nucleic acid molecule (e.g., primer) or nucleoside triphosphates. Simple oligoamides also can be used. Numerous other possibilities, in addition to those mentioned above, can be performed by one skilled in the art.

Different mass or mobility modified primers allow for multiplex sequencing via simultaneous detection of primer-modified Sanger sequencing ladders. Mass or mobility modifications can be incorporated during the amplification process through nucleoside triphosphates or modified primers.

For use with certain detection means, such as polyacrylamide gel electrophoresis (PAGE), detectable labels must be used in either the primer (typically at the 5'-end) or in one of the chain extending nucleotides. Using radioisotopes such as $^{32}P$, $^{33}P$, or $^{35}S$ is still the most frequently used technique. After PAGE, the gels are exposed to X-ray films and silver grain exposure is analyzed.

Non-radioactive labeling techniques have been explored and, in recent years, integrated into partly automated DNA sequencing procedures. All these improvements utilize the Sanger sequencing strategy. The fluorescent label can be tagged to the primer (Smith et al., *Nature* 321, 674–679 (1986) and EPO Patent No. 87300998.9; Du Pont De Nemours EPO Application No. 0359225; Ansorge et al. *J. Biochem. Biophys. Methods* 13, 325–32 (1986)) or to the chain-terminating dideoxynucleoside triphosphates (Prober et al. *Science* 238, 336–41 (1987); Applied Biosystems, PCT Application WO 91/05060). Based on either labeling the primer or the ddNTP, systems have been developed by Applied Biosystems (Smith et al., *Science* 235, G89 (1987); U.S. Pat. Nos. 570,973 and 689,013), Du Pont De Nemours (Prober et al. *Science* 238, 336–341 (1987); U.S. Pat. Nos. 881,372 and 57,566), Pharmacia-LKB (Ansorge et al. *Nucleic Acids Res.* 15, 4593–4602 (1987) and EMBL Patent Application DE P3724442 and P3805808.1) and Hitachi (JP 1-90844 and DE 4011991 A1). A somewhat similar approach was developed by Brumbaugh et al. (*Proc. Natl. Sci. USA* 85, 5610–14 (1988) and U.S. Pat. No. 4,729,947). An improved method for the Du Pont system using two electrophoretic lanes with two different specific labels per lane is described (PCT Application W092/02635). A different approach uses fluorescently labeled avidin and biotin labeled primers. Here, the sequencing ladders ending with biotin are reacted during electrophoresis with the labeled avidin which results in the detection of the individual sequencing bands (Brumbaugh et al, U.S. Pat. No. 594,676).

More recently even more sensitive non-radioactive labeling techniques for DNA using chemiluminescence triggerable and amplifyable by enzymes have been developed (Beck, O'Keefe, Coull and Köster, *Nucleic Acids Res.* 17, 5115–5123 (1989) and Beck and Köster, *Anal. Chem.* 62, 2258–2270 (1990)). These labeling methods were combined with multiplex DNA sequencing (Church et al. Science 240, 185–188 (1988) and direct blotting electrophoresis (DBE) (Beck and Pohl, EMBO J., Vol. 3: p 2905–2909 (1984)) to provide for a strategy aimed at high throughput DNA sequencing (Köster et al., Nucleic Acids Res. Symposium Ser. No. 24, 318–321 (1991), University of Utah, PCT Application No. WO 90/15883). However, this strategy still suffers from the disadvantage of being very laborious and difficult to automate.

In automated sequencing, fluorescence labeled DNA fragments are detected during migration through the sequencing gel by laser excitation. Fluorescence label is incorporated during the sequencing reaction via labeled primers or chain extending nucleotides (Smith, L. et. al., Fluorescence detection in automated DNA sequence analysis, Nature 321:674–89 1986), (Knight, P., Automated DNA sequencers, Biotechnology 6:1095–96 1988).

Multiple distinctly labeled primers can be used to discriminate sequencing patterns. For example, four differently labeled sequencing primers specific for the single termination reactions, e.g. with fluorescent dyes and online detection using laser excitation in an automated sequencing device. The use of eight differently labeled primers allow the discrimination of the sequencing pattern from both strands. Instead of labeled primers, labeled ddNTP may be used for detection, if separation of the sequencing fragments derived from both strand is provided. With one biotin labeled primer, sequencing fragments from one strand can be isolated for example via biotin-streptavidin coated magnetic beads. Possible is also the isolation via immunoaffinity chromatography in the case of a digoxigenin labeled primer or with affinity chromatography in case of complementary oligonucleotides bound to a solid support.

Another aspect of this invention concerns kits for directly generating from a nucleic acid template, amplified base specifically terminated fragments. Such kits include combinations of the above-described reactants. For instance, in one embodiment, the kit can comprise: i) a set of chain-elongating nucleotides; ii) a set of chain-terminating nucleotides; and (iii) a first DNA polymerase, which has a relatively low affinity towards the chain terminating nucleotide; and (iv) a second DNA polymerase, which has a relatively high affinity towards the chain terminating nucleotide. The kit can also include appropriate solid supports for capture/purification and buffers as well as instructions for use.

The present invention is further illustrated by the following examples which should not be construed as limiting in any way. The contents of all cited references (including literature references, issued patents, published patent applications (including international patent application Publication Number WO 94/16101, entitled DNA Sequencing by Mass Spectrometry by H. Koester; and international patent application Publication Number WO 94/21822 entitled "DNA Sequencing by Mass Spectrometry Via Exonuclease Degradation" by H. Koester), and co-pending patent applications, (including U.S patent application Ser. No. 08/406,199, entitled DNA Diagnostics Based on Mass Spectrometry by H. Koester), and continuations-in-part of co-pending patent applications (published or unpublished) are hereby expressly incorporated by reference.

Example 1: Direct Nucleic Acid Amplification and Sequencing

Materials and Methods

Bacterial Strains and Plasmids

E. coli K12 strains HB101 and XL 1-Blue (Stratagene, Calif.) were grown in LB broth (Miller, J. (1972) Experiments in Molecular Genetics, Cold Spring Harbor Laboratory, Cold Spring Harbor, N.Y.) supplemented with 100 $\mu$g ampicillin/mL (Binotal, Bayer, Germany). DNA-template used for sequencing was a pOM8 derived recombinant plasmid (Oberbäumer, I. (1986) Gene 49: 81–91 1986) with an 400 BP insert from the rrnB gene of E. coli. The plasmid DNA was purified via Diagen plasmid purification tips-100 (Diagen, Hilden, Germany).

DNA Isolation

The DNA template used in the sequencing reaction was isolated according to the method described by Birnboim and Doly (Birnboim, H. C., and Doly, J. Nucleic Acid Res. 7: 1513–1523 1979) with the improvements of Ish-Horowiczs and Burke (Ish-Horowicz, D., and Burke, J. F. Nucleic Acid Res. 9: 2989–2998 1981).

Sequencing reactions

A control sequencing reaction was perfomed in accordance with the Perkin-Elmer, AmpliTaq FS kit protocol.

A combined nucleic acid amplification and sequencing reaction was performed as follows. The base specific reaction mixtures (A, C, G and T, as described below) each contained a buffered solution of: i) DNA template; ii) two thermostable DNA polymerases, each with a different affinity to the ddNTP; iii) the ddNTP; iv) all 4 dNTPs (Pharmacia, Freiburg, Germany); a pair of sequence specific oligonucleotide primers, one of them labeled with a fluorescent dye. The reaction mixture was overlayed with wax.

The sequencing reaction was carried out as follows:

A-reaction: 4 $\mu$l 8 $\mu$M ddATP, 80 $\mu$M each dATP, dCTP, 7-deaza-dGTP, dTTP, 500 mM Tris-HC1 (pH 9.0 at 25° C.), 25 mM MgCl$_2$ containing 1 pmol JOE dye primer, thermal stable pyrophosphatase and 1.6 U AmpliTaq DNA polymerase, FS. To this 50 ng of the DNA template as prepared above (1 $\mu$), 1 U of Taq DNA polymerase (1 $\mu$l) and 10 pmol reverse primer (0.5 $\mu$l) were pipetted.

C-reaction: 4 $\mu$l 8 $\mu$M ddCTP, 80 $\mu$M each dATP, dCTP, 7-deaza-dGTP, dTTP, 500 mM Tris-HC1 (pH 9.0 at 25° C.), 25 mM MgCl$_2$ containing 1 pmol FAM dye primer, thermal stable pyrophosphatase and 1.6 U AmpliTaq DNA polymerase, FS. To this 50 ng of the DNA template (1 $\mu$l), 1 U of Taq DNA polymerase (1 $\mu$l) and 10 pmol reverse primer (0.5 $\mu$l) were pipetted.

G-reaction: 8 $\mu$l 8 $\mu$M ddGTP, 80 $\mu$M each dATP, dCTP, 7-deaza-dGTP, dTTP, 500 mM Tris-HC1 (pH 9.0 at 25° C.) 25 mM MgCl$_2$ containing 1 pmol TAMRA dye primer, thermal stable pyrophosphatase and 1.6 U AmpliTaq DNA polymerase, FS. To this 50 ng of the DNA template (1 $\mu$p), 1 U of Taq DNA polymerase (1 $\mu$l) and 10 pmol reverse primer (0.5 $\mu$l) were pipetted.

T-reaction: 8 $\mu$l 8 $\mu$M ddTTP, 80 $\mu$M each dATP, dCTP, 7-deaza-dGTP, dTTP, 500 mM Tris-HC1 (pH 9.0 at 25° C.), 25 mM MgCl$_2$ containing 1 pmol ROX dye primer, thermal stable pyrophosphatase and 1.6 U AmpliTaq DNA polymerase, FS. To this 50 ng of the DNA template (1 $\mu$l), 1 U of Taq DNA polymerase (1 $\mu$l) and 10 pmol reverse primer (0.5 $\mu$l ) were pipetted.

The incubation conditions included an initial denaturation step of 4 min. 95° C., followed by 15 cycles of 30 sec. 95° C., 30 sec. 52° C., 60 sec. 72° C. The reaction is completed by additional 15 cycles of 30 sec. 95° C., 30 sec. 52° C., 60 sec. 72°°C.

The reaction mixture was separated from the wax by pipetting and ethanol precipitated. The samples were run on an automated ABI prism sequencer model 377.

RESULTS

Figure 2:
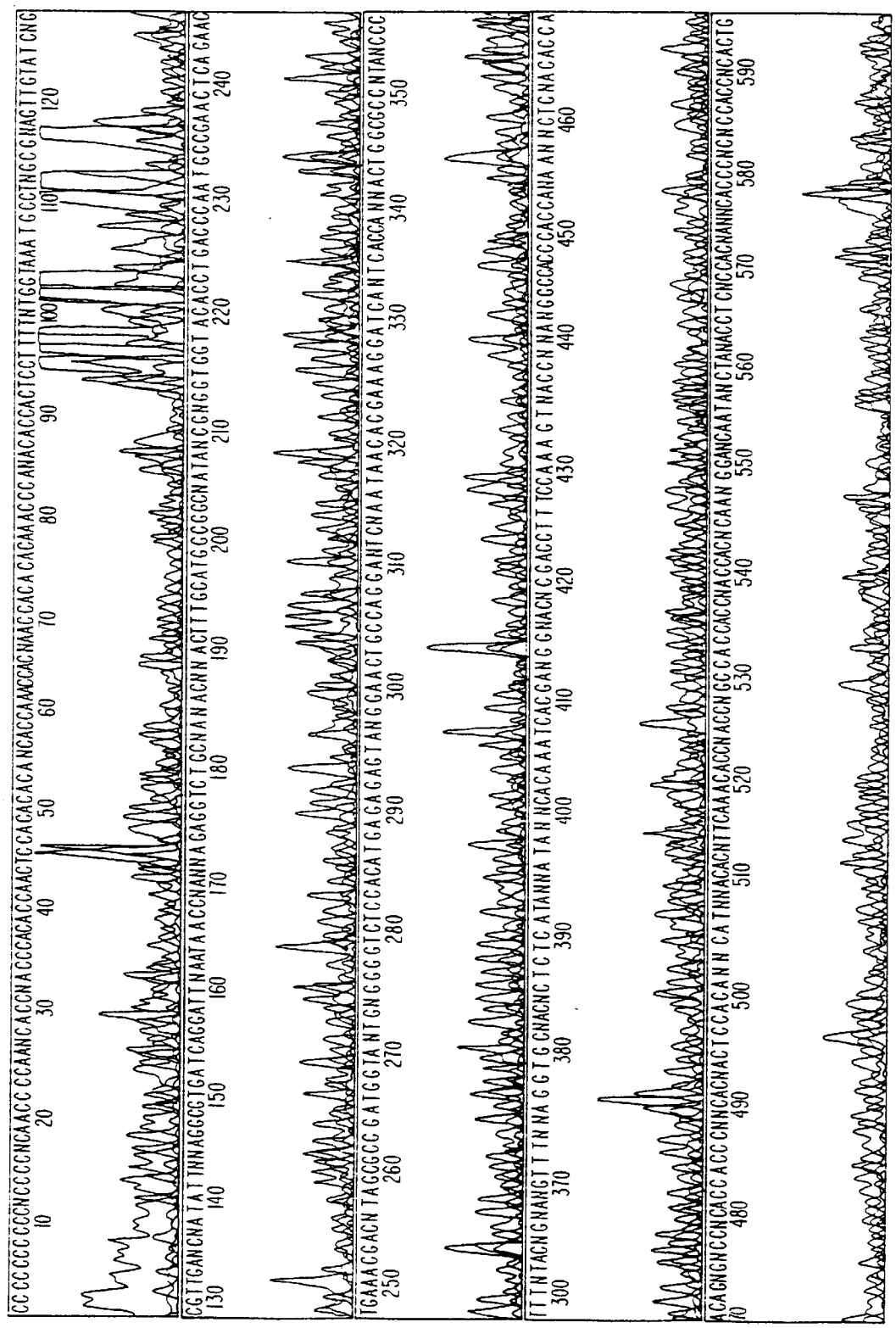
FIG. 2 shows sequence data from an ABI-Prism automated sequencer (Model 373A) again using the p0M8 derived recombinant plasmid with a 400 BP insert of from the rrnB gene of *E. coli*. However, because the sequencing reaction was carried out using standard sequencing protocols on a small amount of template (50 ng), no reliable sequence was obtained.

As can be seen from FIGS. 1 and 2, while the combined amplification and sequencing reaction yielded a 440 BP readable sequence with 50 μg of template DNA (FIG. 1), no sequence data was obtained employing the same amount of template DNA and using the standard cycle sequencing protocol (FIG. 2).

Equivalents

Those skilled in the art will recognize or be able to ascertain using no more than routine experimentation numerous equivalents to the specific procedures described herein. Such equivalents are considered to be within the scope of this invention and are covered by the following claims.

---

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 469 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

```
NTNANCTGCA GCCAAGCTTG GNTGTNTTNG CGGATGAGAG AAGATTTTCA GCCTGATACA      60

GATTAAATCA ACGCAGAAGC GGTCTGATAA AACAGAATTN NCCTGGCGGC AGTAGCGCGG     120

TGGTCCCACC TGACCCCATG CCGAACTCAG AAGTGAAACG CACGTAGCGC CGATGGNANT     180

NTAGGGTCTC CCCATGCGAG AGTAAGGAAC TGCCAGGCAT CAAATAAAAN GAAAGGCTCA     240

GTCGAAAGAC TGGGCCTTTC GTTTTATCTG TTGTTTGTCG GTGAACGCTC TCCTGAGTAG     300

GACAAATCCG CCGGGAGCGG ATTTGAACGT TGCGAAGGGN CNCCCGGAGG NTGGCGGGCA     360

GGACGCCCGC CAATAAACTG CCAGGGCATT CAAATTTAAG CCGNAAGGCC ATTCCTGACG     420

GGATGGGAAT TCGTAATCTG GGTCATGCTA TATGNGACCC ACNNNNNAN                469
```

(2) INFORMATION FOR SEQ ID NO:2:

(i) SEQUENCE CHARACTERISTICS:
        (A) LENGTH: 595 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

```
CCCCCCCCCC CNCCCCACAA CCCCAANCAC CNACCCACAC CAACTCCACA CACANCACCA      60

AACCACNAAC CACACACAAA CCCANACACC ACTCCTTTTN TGGTAAATGC CTNGCGNAGT     120

TGTATCNGCG TTGANCNATA TTNNAGGCGT GATCAGGATT NAATAACCNA NNAGAGGTCT     180

GCNANACNNA CTTTGCATGG CGGCNATANC GNGGTGGTAC ACCTGACCCA ATGCCGAACT     240

CAGAAGTGAA ACGACNTAGC GCCGATGGTA NTGNGGGGTC TCCACATGAG AGAGTANGGA     300

ACTGCCAGGA NTCNAATAAC ACGAAAGGAT CANTCACCAN NACTGGCGCC NTANCCCTTT     360

NTACNGNANG TTTNNAGGTG CNACNCTCTC ATANNATANN CACAAATCAC GANGGNACNC     420

GACCTTTCCA AAGTNACCNN AANGGCCACC CACCANANNC TCNACACCAA CAGNGNCCNC     480

ACCACCCNNC ACNACTCCAC ANNCATNNAC ACNTTCAAAC ACCNACCNGC CACCACCNAC     540

CACNCAAGGG ANCAATANCT ANACCTCNCC ACNANNCACC CNCNCCACCN CACTG         595
```

-continued (2) INFORMATION FOR SEQ ID NO:3:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
GNNNNNNGGN NNNNNNNNNN NNTNNNNNTT TTNNNNNNNA TANTGCCGCA GTCGTTAGGC      60
TCATTTTACA NACACAGCTT TCAAAGGATT TCTTTTTCTG TTAAAACATC TAGGTATCCA     120
AAAGGAGAGT CTAATAAATA CAAATCAGCA TCTTTGTATA CTGCTCTTGC TAAAGAAATT     180
CTTGCTCGTT GATCTCCACT CAGTGTAATT CCACCTTCTC CAAGAACTAT ATTGTCTTTC     240
TCTGCAAACT TGGAGATGTC CTCTTCTAGT TGGCATGCTT TGATGACGCT TCTGTATCTA     300
TATTCATCAT AGGAAACACC AAAGATGATA TTTTCTTTAA TGGTGCCAGG CATAATCCAG     360
GAAAACTGAG AACAGAATGA AATTCTTCCA CTGTGCTTAA TTTTACCCTC TGAAGGCTCC     420
AGTTCTCCCA TAATCATCAT TAGAAGTGAA GTCTTGCCCT GCTCCAGTGG ATCCGTCGAC     480
CTGCAGCCAA TTGGCGTAAT CATGGTCATA GCTGTTTCCC ANNAANNNNN NNNNNNNNNN     540
NNNNNNNNNN NNNNNNNN                                                  558
```

(2) INFORMATION FOR SEQ ID NO:4:

(i) SEQUENCE CHARACTERISTICS:
        (A) LENGTH: 551 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

```
GNNNGNGNNT NNNCNTNCNN GATNTATTTT GGCTGCATGG CCACTTACCA CTNGAGCAGG      60
CAAGAGTNCA CTTCTAATGA TGATTATGGG AGAACTGGAG CCTTCAGAGG GTAAAATTAA     120
GCACAGTGGA AGAATTTCAT TCTGTTCTCA GTTTTCCTGG ATTATGCCTG GCACCATTAA     180
AGAAAATATC ATCTTTGGTG TTTCCTATGA TGAATATAGA TACAGAAGCG TCATCAAAGC     240
ATGCCAACTA GAANAGGACA TCTCCAAGTT TGCAGAGAAA GACAATATAG TTCTTGGAGA     300
AGGTGGAATT ACACTGAGTG GAGATCAACG AGCAAGAATT TCTTTAGCAA GAGCAGTATA     360
CAAAGATGCT GATTTGTATT TATTAGACTC TCCTTTTGGA TACCTAGATT TTTTAACAGA     420
AAAAGAAATA TTTGAAAGCT GTGTCTGTAA ACTGATGGCT AACGGGCTGC AGGAATTCAC     480
TGGCCGTCGT TTTANAAAAN NAGGGGNNGN NNNNNNNNNN NNNNNNNNNN NNNNNNNNNN     540
NNNNNNNNNN N                                                         551
```

We claim:

1. A kit for obtaining amplified and chain terminated nucleic acid molecules from a nucleic acid template comprising; i) a set of chain-elongating nucleotides; ii) at least one chain-terminating nucleotide; iii) a first polymerase; and iv) a second polymerase, which has a higher affinity towards at least one chain terminating nucleotide relative to the first polymerase.

2. A kit of claim 1, which additionally comprises a primer and a restriction enzyme that can cleave the primer.

3. A kit of claim 1, wherein the first and second polymerases are thermostable DNA polymerases.

4. A kit of claim 3, wherein the thermostable DNA polymerases are selected from the group consisting of: Taq DNA polymerase, AmpliTaq FS DNA polymerase, Deep Vent (exo⁻) DNA polymerase, Vent DNA polymerase, Vent (exo⁻) DNA polymerase and Deep Vent DNA polymerases, Thermo Sequenase, exo(-) *Pseudococcus furiosus* (Pfu) DNA polymerase, AmpliTaq, Ultman, 9 degree Nm, Tth, Hot Tub, *Pyrococcus furiosus* (Pfu), and *Pyrococcus woesei* (Pwo) DNA polymerase.

5. A kit of claim 1, wherein the set of chain-elongating nucleotides is selected from the group consisting of; i) at least one deoxyadenosine triphosphate; ii) at least one deoxyguanosine triphosphate; iii) at least one deoxycytidine triphosphate; and iv) at least one thymidine triphosphate.

6. A kit of claim 5, wherein the deoxyadenosine and/or the deoxyguanosine is an N7- or N9- deazapurine nucleotide.

7. A kit of claim 1, wherein the chain terminating nucleotide is selected from the group consisting of: 2',3'-dideoxyadenosine triphosphate, 2',3'-dideoxyguanosine triphosphate, 2',3'-dideoxycytidine triphosphate, and 2',3'-dideoxythymidine triphosphate.

8. A kit of claim 1, which additionally includes at least one primer.

9. A kit of claim 8, wherein the primer is linked to a solid support.

10. A kit of claim 9, wherein the solid support is selected from the group consisting of beads, capillaries, flat supports, membranes and wafers.

11. A kit of claim 8 or 9, wherein the primer contains a restriction site or a ribonucleotide.

12. A kit of claim 8, wherein the primer is mass modified and the amplified and chain terminated nucleic acid molecules are detected by mass spectrometry.

13. A kit of claim 8, wherein the primer is mobility modified and the amplified and chain terminated nucleic acid molecules are detected by electrophoresis.

14. A kit of claim 7, wherein at least one chain terminating nucleotide is mass modified and the amplified and chain terminated nucleic acid molecules are detected by mass spectrometry.

15. A kit of claim 1, which additionally comprises a proof reading DNA polymerase.

16. A kit of claim 1, which additionally comprises a reverse transcriptase.

17. A process for simultaneously amplifying and sequencing a single stranded nucleic acid molecule, comprising the steps of:

a) contacting the single stranded nucleic acid molecule with: i) at least one primer that can hybridize to the single stranded nucleic acid molecule, (ii) a set of chain elongating nucleotides, (iii) at least one chain terminating nucleotide, (iv) a first DNA polymerase; and (v) a second DNA polymerase, which has a higher affinity towards the chain terminating nucleotide relative to the first polymerase, so that polymerization by the first polymerase results in amplification and polymerization by the second polymerase results in the formation of chain terminated fragments;

b) detecting the chain terminated fragments by a detection means; and c) aligning the fragments to determine the sequence of the single stranded nucleic acid molecule.

18. A process of claim 17, wherein the first and second polymerases are thermostable DNA polymerases.

19. A process of claim 17, wherein the set of chain-elongating nucleotides is selected from the group consisting of: i) at least one deoxyadenosine triphosphate; ii) at least one deoxyguanosine triphosphate; iii) at least one deoxycytidine triphosphate; and iv) at least one thymidine triphosphate.

20. A process of claim 19, wherein the deoxyadenosine and/or the deoxyguanosine is an N7- or N9- deazapurine nucleotide.

21. A process of claim 17, wherein the chain terminating nucleotide is selected from the group consisting of 2',3'-dideoxyadenosine triphosphate, 2',3'-dideoxyguanosine triphosphate, 2',3'-dideoxycytidine triphosphate, and 2',3'-dideoxythymidine triphosphate.

22. A process of claim 17, wherein the detection means is a separation means selected from the group consisting of: polyacrylamide gel electrophoresis, capillary zone electrophoresis and mass spectrometry in conjunction with a visualization means selected from the group consisting of: colorimetry, fluorimetry, chemiluminescence, radioactivity and mass spectrometry.

23. A process of claim 17, wherein the detection means is mass spectrometry.

24. A process of claim 23, wherein the mass spectrometry is performed using an ion source selected from the group consisting of: matrix assisted laser desorption ionization (MALDI), electrospray (ES), ionspray, thermospray and massive cluster impact; and a detection format selected from the group consisting of: time-of-flight; quadrupole, magnetic sector, Fourier transform ion cyclotron resonance and ion trap.

25. A process of claim 17, wherein the single stranded DNA molecule has been synthesized from RNA using a reverse transcriptase.

26. A process of claim 17, wherein the primer is linked to a solid support.

27. A process of claim 26, wherein the solid support is selected from the group consisting of: beads, capillaries, flat supports, membranes and wafers.

28. A process of claim 17 or 26, wherein the primer contains a restriction site or a ribonucleotide.

29. A process of claim 17 or 26, wherein the primer is mass modified and the amplified and chain terminated fragments are detected by mass spectrometry.

30. A process of claim 17 or 26, wherein the primer is mobility modified and the amplified and chain terminated fragments are detected by electrophoresis.

31. A process of claim 17 or 26, wherein at least one chain terminating nucleotide is mass modified and the amplified and chain terminated fragments are detected by mass spectrometry.

32. A process of claim 17, which additionally comprises a proofreading DNA polymerase.

33. A process for simultaneously amplifying and sequencing a nucleic acid molecule, comprising the steps of:

a) denaturing a double stranded DNA molecule to obtain two complementary single stranded DNA molecules;

b) contacting at least one of the single stranded DNA molecules with a complementary primer to obtain at least one primer containing single stranded DNA molecule;

c) contacting the at least one primer containing single stranded DNA molecule with: (i) a set of chain elongating nucleotides, (ii) at least one chain terminating nucleotide, (iii) a first DNA polymerase; and (iv) a second DNA polymerase, which has a higher affinity towards the chain terminating nucleotide relative to the first polymerase, so that polymerization by the first polymerase results in amplification and polymerization by the second polymerase results in the formation of chain terminated fragments;

d) repeating steps a) through c) for an appropriate number of times to obtain chain terminated fragments for detection; and e) detecting the chain terminated fragments by a detection means and aligning the fragments to determine the sequence of the nucleic acid molecule.

34. A process of claim 33, wherein the first and second polymerases are thermostable DNA polymerases.

35. A process of claim 33, wherein the set of chain-elongating nucleotides is selected from the group consisting of: i) at least one deoxyadenesine triphosphate; ii) at least one deoxyguanosine triphosphate; iii) at least one deoxycytidine triphosphate; and iv) at least one thymidine triphosphate.

36. A process of claim 35, wherein the deoxyadenosine and/or the deoxyguanosine is an N7- or N9- deazapurine nucleotide.

37. A process of claim 33, wherein the chain terminating nucleotide is selected from the group consisting of 2',3'-dideoxyadenosine triphosphate, 2',3'-dideoxyguanosine triphosphate, 2',3'-dideoxycytidine triphosphate, and 2',3'-dideoxythymidine triphosphate.

38. A process of claim 33, wherein the detection means is a separation means selected from the group consisting of: polyacrylamide gel electrophoresis, capillary zone electrophoresis and mass spectrometry, in conjunction with a visualization means selected from the group consisting of: colorimetry, fluorimetry, chemiluminescence, radioactivity, and mass spectrometry.

39. A process of claim 33, wherein the detection means is mass spectrometry.

40. A process of claim 39, wherein the mass spectrometry is performed using an ion source selected froni the group consisting of: matrix assisted laser desorption ionization (MALDI), electrospray (ES), ionspray, thermospray and massive cluster impact, and a detection format selected from the group consisting of time-of-flight; quadrupole, magnetic sector, Fourier transform ion cyclotron resonance and ion trap.

41. A process of claim 33, wherein the double stranded DNA molecule has been synthesized from RNA using a reverse transcriptase.

42. A process of claim 33, wherein the primer is linked to a solid support.

43. A process of claim 42, wherein the solid support is selected from the group consisting of beads, capillaries, flat supports, membranes and wafers.

44. A process of claim 33 or 42, wherein the primer contains a restriction site or a ribonucleotide.

45. A process of claim 33 or 42, wherein the primer is mass modified and the amplified and chain terminated fragments are detected by mass spectrometry.

46. A process of claim 33 or 42, wherein the primer is mobility modified and the amplified and chain terminated fragments are detected by electrophoresis.

47. A process of claim 33, wherein a chain terminating nucleotide is weight modified.

48. A process of claim 33, which additionally comprises a proofreading DNA polymerase.

* * * * *

UNITED STATES PATENT AND TRADEMARK OFFICE
CERTIFICATE OF CORRECTION

PATENT NO. : 5,928,906                   Page 1 of 3
DATED       : July 27, 1999
INVENTOR(S) : Koster et al.

It is certified that error appears in the above-identified patent and that said Letters Patent is hereby corrected as shown below:

at columns 13 to 16, please replace the Sequence Listing with the following Sequence Listing;

SEQUENCE LISTING (1) GENERAL INFORMATION (iii) NUMBER OF SEQUENCES: 2

(2) INFORMATION FOR SEQ ID NO:1:

(i) SEQUENCE CHARACTERISTICS:
      (A) LENGTH: 469 base pairs
      (B) TYPE: nucleic acid
      (C) STRANDEDNESS: single
      (D) TOPOLOGY: linear (ii) MOLECULE TYPE: Genomic DNA (xi) SEQUENCE DESCRIPTION: SEQ ID NO:1:

```
NTNANCTGCA GCCAAGCTTG GNTGTNTTNG CGGATGAGAG AAGATTTTCA GCCTGATACA    60
GATTAAATCA ACGCAGAAGC GGTCTGATAA AACAGAATTN NCCTGGCGGC AGTAGCGCGG   120
TGGTCCCACC TGACCCCATG CCGAACTCAG AAGTGAAACG CACGTAGCGC CGATGGNANT   180
NTAGGGTCTC CCCATGCGAG AGTAAGGAAC TGCCAGGCAT CAAATAAAAN GAAAGGCTCA   240
GTCGAAAGAC TGGGCCTTTC GTTTTATCTG TTGTTTGTCG GTGAACGCTC TCCTGAGTAG   300
GACAAATCCG CCGGGAGCGG ATTTGAACGT TGCGAAGGGN CNCCCGGAGG NTGGCGGGCA   360
GGACGCCCGC CAATAAACTG CCAGGGCATT CAAATTTAAG CCGNAAGGCC ATTCCTGACG   420
GGATGGGAAT TCGTAATCTG GGTCATGCTA TATGNGACCC ACNNNNNAN              469
```

(2) INFORMATION FOR SEQ ID NO:2:

(i) SEQUENCE CHARACTERISTICS:
      (A) LENGTH: 595 base pairs
      (B) TYPE: nucleic acid
      (C) STRANDEDNESS: single
      (D) TOPOLOGY: linear

UNITED STATES PATENT AND TRADEMARK OFFICE
CERTIFICATE OF CORRECTION

PATENT NO.  : 5,928,906
DATED       : July 27, 1999
INVENTOR(S) : Koster et al.

Page 2 of 3

It is certified that error appears in the above-identified patent and that said Letters Patent is hereby corrected as shown below:

(ii) MOLECULE TYPE: Genomic DNA (xi) SEQUENCE DESCRIPTION: SEQ ID NO:2:

| | | | | | | |
|---|---|---|---|---|---|---|
| CCCCCCCCCC | CNCCCCACAA | CCCCAANCAC | CNACCCACAC | CAACTCCACA | CACANCACCA | 60 |
| AACCACNAAC | CACACACAAA | CCCANACACC | ACTCCTTTTN | TGGTAAATGC | CTNGCGNAGT | 120 |
| TGTATCNGCG | TTGANCNATA | TTNNAGGCGT | GATCAGGATT | NAATAACCNA | NNAGAGGTCT | 180 |
| GCNANACNNA | CTTTGCATGG | CGGCNATANC | GNGGTGGTAC | ACCTGACCCA | ATGCCGAACT | 240 |
| CAGAAGTGAA | ACGACNTAGC | GCCGATGGTA | NTGNGGGGTC | TCCACATGAG | AGAGTANGGA | 300 |
| ACTGCCAGGA | NTCNAATAAC | ACGAAAGGAT | CANTCACCAN | NACTGGCGCC | NTANCCCTTT | 360 |
| NTACNGNANG | TTTNNAGGTG | CNACNCTCTC | ATANNATANN | CACAAATCAC | GANGGNACNC | 420 |
| GACCTTTCCA | AAGTNACCNN | AANGGCCACC | CACCANANNC | TCNACACCAA | CAGNGNCCNC | 480 |
| ACCACCCNNC | ACNACTCCAC | ANNCATNNAC | ACNTTCAAAC | ACCNACCNGC | CACCACCNAC | 540 |
| CACNCAANGG | ANCAATANCT | ANACCTCNCC | ACNANNCACC | CNCNCCACCN | CACTG | 595 |

IN THE CLAIMS:

Please replace claim 40 with the following claim:

—40. A process of claim 39, wherein the mass spectroscopy is performed using an ion source selected from the group consisting of: matrix assisted laser desorption ionization (MALDI), electrospray (ES), ionspray, thermospray and massive cluster impact, and a detection format

UNITED STATES PATENT AND TRADEMARK OFFICE
CERTIFICATE OF CORRECTION

PATENT NO. : 5,928,906
DATED : July 27, 1999
INVENTOR(S) : Koster et al.

It is certified that error appears in the above-identified patent and that said Letters Patent is hereby corrected as shown below:

selected from the group consisting of time-of-flight; quadrupole, magnetic sector, Fourier transform ion cyclotron resonance and ion trap.--

Signed and Sealed this

Thirteenth Day of June, 2000

Attest:

Q. TODD DICKINSON

*Attesting Officer*      *Director of Patents and Trademarks*